US011141432B2

(12) United States Patent
Shrikant et al.

(10) Patent No.: US 11,141,432 B2
(45) Date of Patent: Oct. 12, 2021

(54) MATERIALS AND METHODS FOR INCREASING IMMUNE RESPONSES

(71) Applicant: Mayo Foundation for Medical Education and Research, Rochester, MN (US)

(72) Inventors: Protul Shrikant, Scottsdale, AZ (US); Leena Chaudhuri, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 360 days.

(21) Appl. No.: 16/081,298

(22) PCT Filed: Mar. 2, 2017

(86) PCT No.: PCT/US2017/020347
§ 371 (c)(1),
(2) Date: Aug. 30, 2018

(87) PCT Pub. No.: WO2017/151855
PCT Pub. Date: Sep. 8, 2017

(65) Prior Publication Data
US 2019/0076475 A1    Mar. 14, 2019

Related U.S. Application Data

(60) Provisional application No. 62/303,259, filed on Mar. 3, 2016.

(51) Int. Cl.
*A61K 35/17*    (2015.01)
*A61K 38/20*    (2006.01)
(Continued)

(52) U.S. Cl.
CPC ............ *A61K 35/17* (2013.01); *A61K 31/352* (2013.01); *A61K 31/713* (2013.01);
(Continued)

(58) Field of Classification Search
None
See application file for complete search history.

(56) References Cited

U.S. PATENT DOCUMENTS

2010/0278873 A1\*  11/2010  Avigan ................... A61P 35/00
424/277.1

FOREIGN PATENT DOCUMENTS

WO        2008150388      \* 12/2008
WO    WO 2008/150388        12/2008
(Continued)

OTHER PUBLICATIONS

Pozza et al., Biochimica et Biophysica Acta. 2012. vol. 1823, pp. 1856-1863 (Year: 2012).\*
(Continued)

*Primary Examiner* — Karl J Puttlitz
(74) *Attorney, Agent, or Firm* — Fish & Richardson P.C.

(57) ABSTRACT

Provided herein are materials and methods for treating a cancer and/or an infection in a mammal. One or more mitochondrial protein uncoupling protein 2 (UCP2) inhibitors can be administered to a mammal to enhance an immune response produced against an antigen (e.g., a tumor associated antigen or a pathogen associated antigen) present within the mammal.

15 Claims, 18 Drawing Sheets

Specification includes a Sequence Listing.

(51) Int. Cl.
| | |
|---|---|
| C12N 5/0783 | (2010.01) |
| A61K 39/00 | (2006.01) |
| A61K 31/352 | (2006.01) |
| A61K 31/713 | (2006.01) |
| A61P 31/18 | (2006.01) |
| A61P 35/00 | (2006.01) |
| A61K 39/12 | (2006.01) |

(52) U.S. Cl.
CPC ........ *A61K 38/208* (2013.01); *A61K 39/0011* (2013.01); *A61K 39/12* (2013.01); *A61P 31/18* (2018.01); *A61P 35/00* (2018.01); *C12N 5/0638* (2013.01); *A61K 2039/5158* (2013.01); *A61K 2039/876* (2018.08); *C12N 2501/999* (2013.01)

(56) References Cited

FOREIGN PATENT DOCUMENTS

| | | | |
|---|---|---|---|
| WO | 2010151517 | * | 12/2010 |
| WO | WO 2010/151517 | | 12/2010 |

OTHER PUBLICATIONS

Arsenijevic et al., "Disruption of the uncoupling protein-2 gene in mice reveals a role in immunity and reactive oxygen species production," Nature genetics, 26:435-439, Dec. 2000.
Ayyasamy et al., "Cellular Model of Warburg Effect Identifies Tumor Promoting Function of UCP2 in Breast Cancer and Its Suppression by Genipin," PLoS ONE., 6(9):e24792, Sep. 2015.
Bai et al., "Persistent nuclear factor-kappa B activation in Ucp2-/- mice leads to enhanced nitric oxide and inflammatory cytokine production," The Journal of biological chemistry, 280:19062-19069, May 2005.
Ball et al., "Uncoupling protein 2 negatively regulates mitochondrial reactive oxygen species generation and induces phosphatase-mediated anti-inflammatory response in experimental visceral leishmaniasis," J. Immunol., 187(3):1322-32, Aug. 2011.
Buck et al., "T cell metabolism drives immunity," J. Exp. Med., 212(9):1345-1360, Aug. 2015.
Chaudhuri et al., "Uncoupling protein 2 regulates metabolic reprogramming and fate of antigen-stimulated CD8+ T cells," Cancer Immunology, Immunotherapy, 65(7):869-74, Jul. 2016.
Criscuolo et al., "UCP2, UCP3, avUCP, what do they do when proton transport is not stimulated? Possible relevance to pyruvate and glutamine metabolism," Biochimica et biophysica. acta., 1757:1284-1291, Sep. 2006.
Emre and Nübel, "Uncoupling protein UCP2: When mitochondrial activity meets immunity," FEBS. Letters, 584(8):1437-1442, Apr. 2010.
Gattinoni et al., "Wnt signaling arrests effector T cell differentiation and generates CD8+ memory stem cells," Nat. Med., 15:808-813, Jul. 2009.
GenBank® Accession No. AAC51336.1, "UCP2 [*Homo sapiens*]," dated Jun. 2, 1997, 1 page.
GenBank® Accession No. NM_003355, "*Homo sapiens* uncoupling protein 2 (UCP2), mRNA," Apr. 30, 2016, 5 pages.
GenBank® Accession No. U76367.1, "Human uncoupling protein-2 (UCP2) mRNA, nuclear gene encoding mitochondrial protein, complete cds," dated May 15, 2001, 2 pages.
GenBank® Accession No. U82819.1, "*Homo sapiens* UCP2 mRNA, complete cds," dated Jun. 3, 1997, 2 pages.
GenBank® accession No. NP_003346, "mitochondrial uncoupling protein 2 [*Homo sapiens*]," Apr. 30, 2016, 4 pages.
Jeffords et al., "Tailoring Material Properties of Cardiac Matrix Hydrogels to Induce Endothelial Differentiation of Human Mesenchymal Stem Cells," ACS applied materials & interfaces, 7(20): 11053-11061, May 2015.
Joseph et al., "The mitochondrial citrate/isocitrate carrier plays a regulatory role in glucose-stimulated insulin secretion," The Journal of biological chemistry, 281:35624-35632, Nov. 2006.
Kaminski et al., "Novel role for mitochondria: protein kinase Ctheta-dependent oxidative signaling organelles in activation-induced T-cell death," Molecular and cellular biology, 27:3625-3639, May 2007.
Kim et al., "Genipin attenuates sepsis-induced immunosuppression through inhibition of T lymphocyte apoptosisw," International Immunopharmacology, 27(1):15-23, Jul. 2015.
Kizaki et al., "Uncoupling protein 2 plays an important role in nitric oxide production of lipopolysaccharide-stimulated macrophages," Proceedings of the National Academy of Sciences of the United States of America, 99:9392-9397, Jul. 2002.
Kwon et al., "Genipin, a cross-linking agent, promotes odontogenic differentiation of human dental pulp cells," J. Endod., 41(4):501-7, Apr. 2015.
Locasale and Cantley, "Metabolic flux and the regulation of mammalian cell growth," Cell metabolism, 14:443-451, Oct. 2011.
Lunt and Vander Heiden, "Aerobic glycolysis: meeting the metabolic requirements of cell proliferation," Annu. Rev. Cell. Dev. Biol., 27:441-464, Nov. 2011.
MacIver et al., "Metabolic regulation of T lymphocytes," Annual review of immunology, 31:259-283, Mar. 2013.
Marr et al., "Leishmania donovani infection causes distinct epigenetic DNA methylation changes in host macrophages," PLoS Pathog, 10(10):e1004419, Oct. 2014.
Patsoukis et al., "PD-1 alters T-cell metabolic reprogramming by inhibiting glycolysis and promoting lipolysis and fatty acid oxidation," Nat. Commun., 6:6692, Mar. 2015.
PCT International Preliminary Report on Patentability in International Application No. PCT/US2017/020347 dated Sep. 13, 2018, 11 pages.
PCT International Search Report in International Application No. PCT/US2017/020347 dated May 16, 2017, 4 pages.
Pecqueur et al., "UCP2, a metabolic sensor coupling glucose oxidation to mitochondrial metabolism?" IUBMB life, 61:762-767, Jul. 2009.
Pecqueur et al., "Uncoupling protein-2 controls proliferation by promoting fatty acid oxidation and limiting glycolysis-derived pyruvate utilization," FASEB journal: official publication of the Federation of American Societies for Experimental Biology 22:9-18, Jan. 2008.
Pozza et al., "Role of mitochondrial uncoupling protein 2 in cancer cell resistance to gemcitabine," Biochim. Biophys. Acta., 1823(10):1856-63, Oct. 2012.
Rupprecht et al., "Quantification of uncoupling protein 2 reveals its main expression in immune cells and selective up-regulation during T-cell proliferation," PloS one, 7:e41406, Aug. 2012.
Sena et al., "Mitochondria are required for antigen-specific T cell activation through reactive oxygen species signaling," Immunity, 38:225-236, Feb. 2013.
Shrikant, "Uncoupling metabolism for balanced CD8+ T cell differentiation" Presented at LSU Cancer Center on Mar. 4, 2016, 29 pages.
Sukumar et al., "Inhibiting glycolytic metabolism enhances CD8+ T cell memory and antitumor function," The Journal of clinical investigation, 123:4479-4488, Oct. 2013.
Topalian et al., "Immune checkpoint blockade: a common denominator approach to cancer therapy," Cancer cell, 27:450-461, Apr. 2015.
Van der Windt et al., "Mitochondrial respiratory capacity is a critical regulator of CD8+ T cell memory development," Immunity, 36:68-78, Jan. 2012.
Vander Heiden et al., "Understanding the Warburg effect: the metabolic requirements of cell proliferation," Science, 324:1029-1033, May 2009.
Vozza et al., "UCP transports C4 metabolites out of mitochondria, regulating glucose and glutamine oxidation," Proceedings of the National Academy of Sciences of the United States of America, 111:960-965, Jan. 2014.
Wang and Green, "Metabolic checkpoints in activated T cells," Nature immunology,13:907-915, Oct. 2012.

(56) References Cited

OTHER PUBLICATIONS

Weinberg and Chandel, "Mitochondria in the regulation of innate and adaptive immunity," Immunity, 42:406-417, Mar. 2015.
Wherry et al., "Lineage relationship and protective immunity of memory CD8 T cell subsets," Nature immunology, 4:225-234, Mar. 2003.
Zhang et al., "UCP2 regulates energy metabolism and differentiation potential of human pluripotent stem cells," The EMBO journal, 30:4860-4873, Dec. 2011.

\* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: artificial
<220> FEATURE:
<223> OTHER INFORMATION: synthetic OT-1 cognate peptide antigen

<400> SEQUENCE: 1

Ser Ile Ile Asn Phe Glu Lys Leu
1               5
```

MATERIALS AND METHODS FOR INCREASING IMMUNE RESPONSES

CLAIM OF PRIORITY

This application is a National Stage application under 35 U.S.C. § 371 of International Application No. PCT/US2017/020347, having an International Filing Date of Mar. 2, 2017, which claims the benefit of U.S. Patent Application Ser. No. 62/303,259, filed on Mar. 3, 2016. The entire contents of which are hereby incorporated by reference.

TECHNICAL FIELD

This document provides materials and methods related to using one or more mitochondrial protein uncoupling protein 2 (UCP2) inhibitors to enhance an immune response produced against an antigen (e.g., a tumor associated antigen or a pathogen associated antigen).

BACKGROUND

Naïve CD8+ T cells require three cell extrinsic signals; antigen (TCR), co-stimulatory molecules like B7.1 (CD28) and cytokines like IL-12 (IL-12Rb), to activate mTORC1 kinase that provokes a metabolic shift predominantly from fatty acid oxidation (catabolism) to aerobic glycolysis and high oxidative phosphorylation driven by pyruvate usage via the TCA cycle (anabolism) in the mitochondria. The metabolic shift or reprogramming from catabolism to anabolism is required to support growth, proliferation and differentiation of naïve CD8+ T cells resulting in clonal expansion of effector CD8+ T cells (Buck et al., 2015 *J. Experimental Medicine* 212:1345-1360). Following clearance of antigen, majority of the effector CD8+ T cells undergo contraction via apoptosis and only a small fraction of cells persist to form memory.

SUMMARY

Provided herein are materials and methods related to using UCP2 inhibitors to enhance an immune response produced against an antigen (e.g., a tumor associated antigen or a pathogen associated antigen). As demonstrated herein, inhibition UCP2 enhances differentiation of CD8+ T cells. Thus, UCP2 inhibitors can be incorporated into therapeutic schemes to enhance immune responses against, for example, cancers and persisting pathogenic (e.g., viral) infections.

In some aspects, this document provides methods for treating cancer in a mammal. In some cases, the methods can include contacting an antigen, a co-stimulatory molecule, a cytokine, and a UCP2 inhibitor to naïve CD8+ T cells obtained from said mammal to obtain effector CD8+ T cells specific for the antigen, and administering the antigen specific effector CD8+ T cells to said mammal. The cancer can be breast cancer and the antigen can be MUC-1 or ETA. The mammal can be a human. The UCP2 inhibitor can be Genipin or siRNA.

In some aspects, this document also provides methods for treating an infection in a mammal. Such methods can include contacting an antigen, a co-stimulatory molecule, a cytokine, and a UCP2 inhibitor to naïve CD8+ T cells obtained from said mammal to obtain effector CD8+ T cells specific for the antigen, and administering the antigen specific effector CD8+ T cells to said mammal. The infection can be HIV and the antigen can be gp120. The mammal can be a human. The UCP2 inhibitor can be Genipin or siRNA.

In some aspects, this document provides methods for treating cancer in a mammal, the method including identifying said mammal as having cancer, and administering to said mammal a UCP2 inhibitor. The cancer can be breast cancer and the antigen can be MUC-1 or ETA. The mammal can be a human. The UCP2 inhibitor can be Genipin or siRNA. The method can also include administering a co-stimulatory molecule (e.g., B7.1). The method can also include administering a cytokine (e.g., IL-12).

In some aspects, this document provides methods for treating an infection in a mammal, the methods including identifying said mammal as having said infection, and administering to said mammal a UCP2 inhibitor. In some cases, the infection can be HIV and said antigen can be gp120. The mammal can be a human. The UCP2 inhibitor can be Genipin or siRNA. The method can also include administering a co-stimulatory molecule (e.g., B7.1). The method can also include administering a cytokine (e.g., IL-12).

In some aspects, this document provides methods of generating antigen specific CD8+ T cells. Such methods include contacting an antigen, a co-stimulatory molecule, a cytokine, and a UCP2 inhibitor to naïve CD8+ T cells obtained from a mammal. The method can also include expanding the antigen specific T cells. The mammal can be a human. In some cases, the mammal has cancer. In some cases, the cancer can be breast cancer and the antigen can be MUC-1 or ETA. In some cases, the mammal has an infection. In some cases, the infection can be HIV and said antigen can be gp120. The UCP2 inhibitor can be Genipin or siRNA. The co-stimulatory molecule can be B7.1. The cytokine can be IL-12. Also provided herein are antigen specific T cells obtained by such methods.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
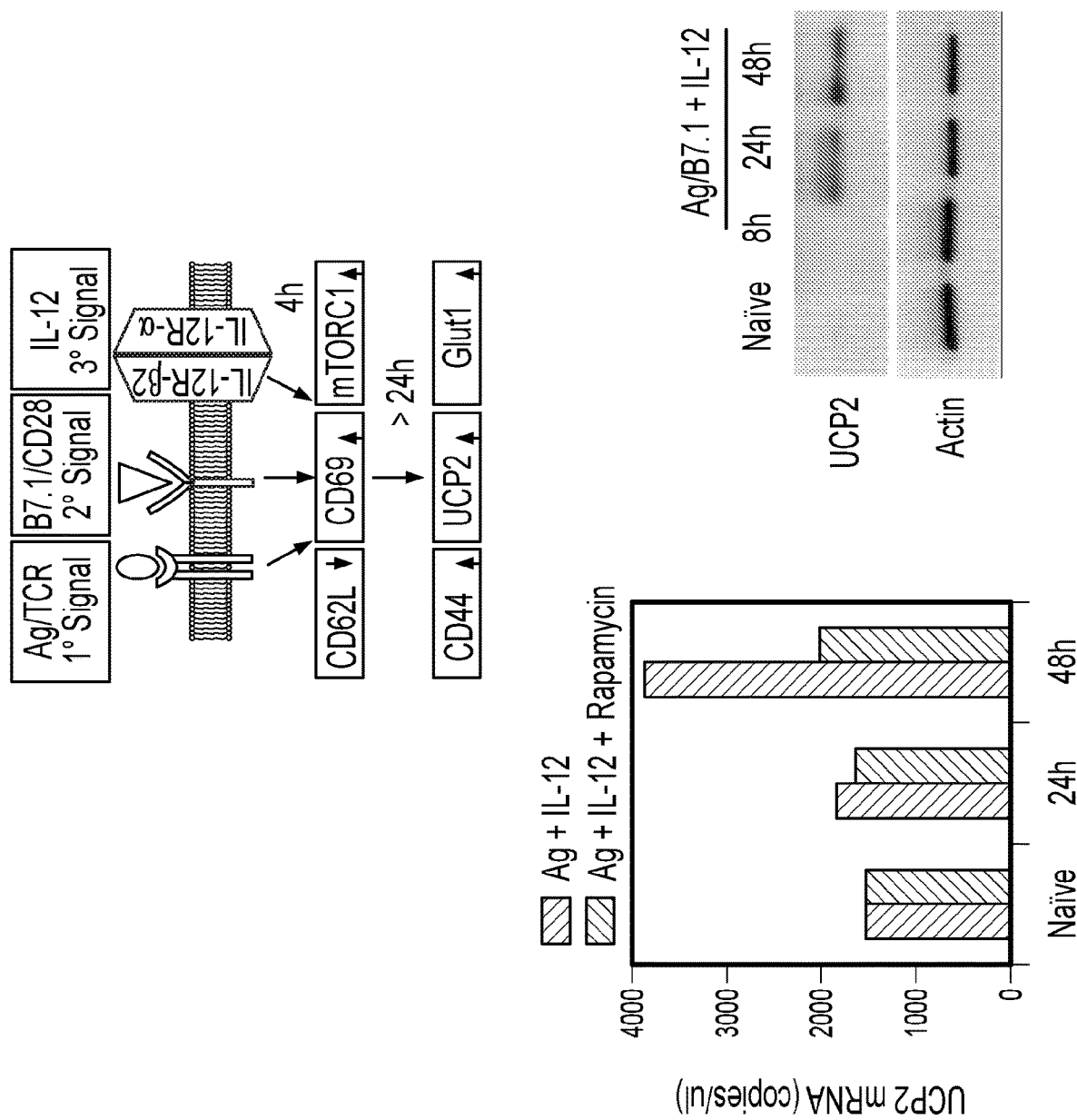
FIG. 1 shows that antigen stimulation induces UCP2 expression in naïve CD8+T cells.
Figure 1:
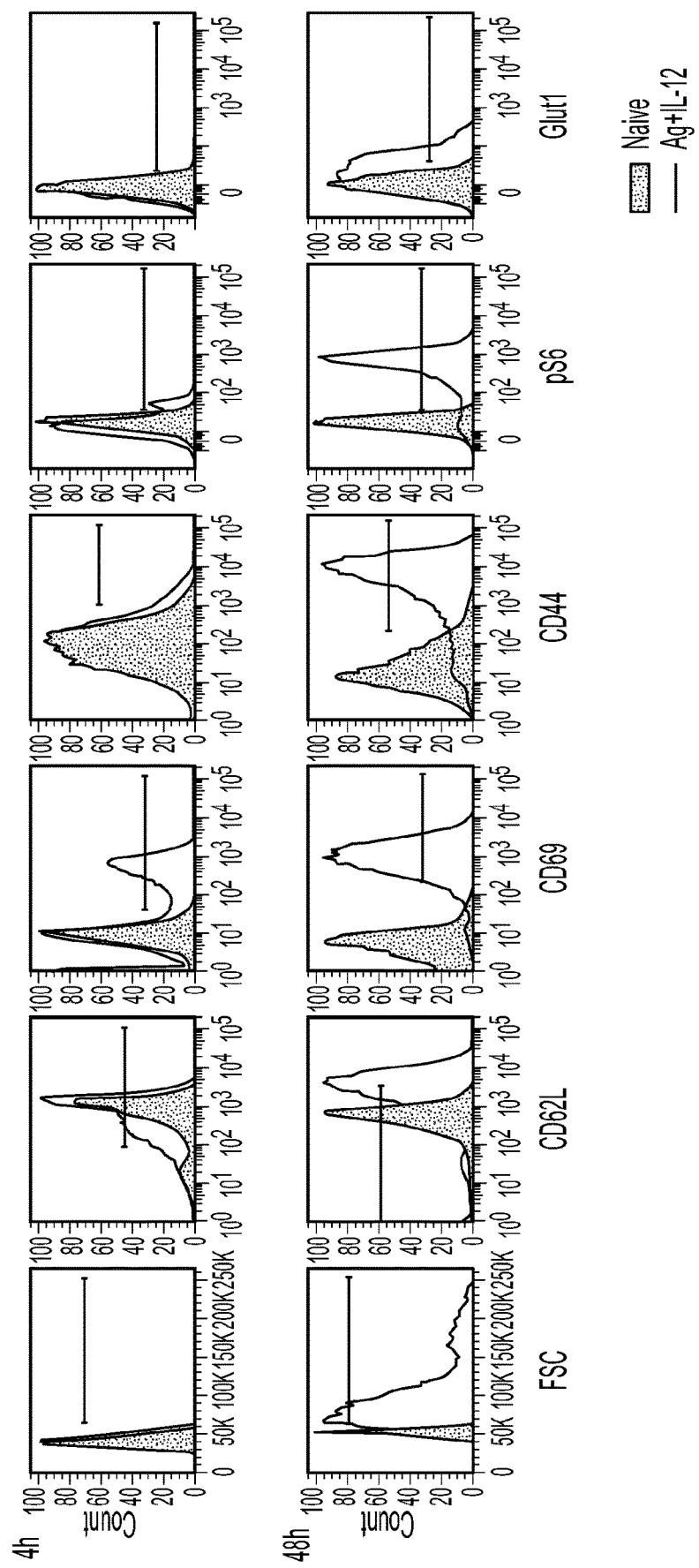

Provided herein are materials and methods for treating a cancer and/or an infection in a mammal using one or more UCP2 inhibitors. For example, a composition including one or more UCP2 inhibitors can be used to increase an immune response to an antigen (e.g., a tumor associated antigen or a pathogen associated antigen) within a mammal. In some cases, a composition including one or more UCP2 inhibitors, a co-stimulatory molecule, a cytokine, and an antigen, can be used to condition antigen specific effector CD8+ T cells ex vivo (e.g., for use in adoptive cell therapy). In some cases, a composition including one or more UCP2 inhibitors (e.g., a vaccine) can be used to increase an antigen specific effector CD8+ T cell immune response in vivo.

A composition including one or more UCP2 inhibitors can increase an immune response to any antigen within the mammal. In some cases, an antigen can be a tumor associated antigen (e.g., an antigenic substance produced by a cancer cell). Examples of tumor associated antigens include, without limitation, alphafetoprotein (AFP; associated with germ cell tumors and/or hepatocellular carcinoma), carcinoembryonic antigen (CEA; associated with bowel cancer, lung cancer, and/or breast cancer), CA-125 (associated with ovarian cancer), MUC-1 (associated with breast cancer), epithelial tumor antigen (ETA; associated with breast cancer), and melanoma-associated antigen (MAGE; associated with malignant melanoma). In some cases, an antigen can be a pathogen associated antigen (e.g., an antigenic substance produced by an infectious agent such as a virus, bacterium, prion, fungus, viroid, or parasite). Examples of pathogen associated antigens include, without limitation, HBsAg (associated with hepatitis B), DENV NS1 proteins (associated with Dengue virus), gp120 (associated with human immunodeficiency virus (HIV)), and hemagglutinin (e.g., $HA_1$ and HA2; associated with the influenza virus).

Any type of mammal having a cancer and/or an infection can be treated as described herein. For example, humans and other primates such as monkeys having a cancer and/or an infection can be treated with a composition including one or more UCP2 inhibitors. In some cases, dogs, cats, horses, cows, pigs, sheep, rabbits, mice, and rats can be treated with one or more UCP2 inhibitors as described herein. Any appropriate method can be used to identify a mammal having a cancer and/or an infection. Once identified as having a cancer and/or an infection, the mammal can be administered or instructed to self-administer a composition including one or more UCP2 inhibitors.

In some cases, a composition including one or more UCP2 inhibitors can be contacted with cells (e.g., naïve CD8+ T cells) obtained from the mammal. For example, a composition including one or more UCP2 inhibitors, a co-stimulatory molecule, a cytokine, and an antigen, can be contacted with naïve CD8+ T cells obtained from the mammal to generate CD8+ T cells specific for the antigen, and the antigen specific CD8+ T cells can be administered to the mammal. In some cases, a composition including one or more UCP2 inhibitors can be administered directly to the mammal.

Any appropriate UCP2 inhibitor can be included in a composition including one or more UCP2 inhibitors. A UCP2 inhibitor can be an inhibitor of UCP2 polypeptide expression or an inhibitor of UCP2 polypeptide activity. An example of a chemical compound that reduces UCP2 polypeptide activity includes, without limitation, Genipin. Examples of compounds that reduce UCP2 polypeptide expression include, without limitation, nucleic acid molecules designed to induce RNA interference (e.g., an RNAi molecule or a siRNA molecule), antisense molecules, and miRNAs. siRNA molecules can be readily designed based upon the nucleic acid sequences of UCP2. Examples of a UCP2 nucleic acids include, without limitation, the human UCP2 sequence set forth in GenBank® Accession No. NM_003355 (GI No. 13259540), GenBank® Accession No. HSU76367 (GI No. 1857277), and GenBank® Accession No. HSU82819 (GI No. 1877473). Additional UCP2 inhibitors can be readily designed based upon the polypeptide sequences of UCP2. Examples of UCP2 polypeptides include, without limitation, the human UCP2 polypeptide having the amino acid sequence set forth in GenBank® accession number NP_003346 (GI No. 13259541) and GenBank® accession number AAC51336 (GI No. 1877474).

In some cases, one or more UCP2 inhibitors (e.g., one, two, three, four, five, or more UCP2 inhibitors) can be administered to a mammal to increase an immune response against an antigen present in the mammal. For example, two or more UCP2 inhibitors can be administered to a mammal (e.g., a human with cancer) to increase an immune response against an antigen present in the mammal (e.g., a tumor associated antigen).

A composition including one or more UCP2 inhibitors can be administered to mammal having a cancer and/or an infection together with one or more additional agents such as a co-stimulatory molecule (e.g., T cell co-stimulatory molecules), a cytokine (e.g., T cell cytokines), and/or an antigen described herein. Examples of T cell co-stimulatory molecules include, without limitation, B7.1, CD28, and inducible co-stimulator (ICOS). Examples of cytokines include, without limitation, IL-12, IL-2, and IFN-γ. Co-stimulatory molecules, cytokines, and/or antigens described herein can be administered, for example, as polypeptides (e.g., short or truncated polypeptides or full length polypeptides), DNA encoding such polypeptides, viral particles designed to express such polypeptides, extracts from whole tumor cell lysates, or dendritic cells loaded with such polypeptides or tumor cell lysates. Examples of tumor polypeptide ligands include, without limitation, altered peptide ligands (APLs), xenogeneic tumor peptides, and heteroclitic tumor peptides.

A composition including one or more UCP2 inhibitors can be administered to a mammal having a cancer and/or an infection as a combination therapy with one or more additional agents used in an immune checkpoint blockade. Agents that can be used in an immune checkpoint blockade include, without limitation, molecules that inhibit the programmed cell death 1 protein (PD-1; e.g., antibodies targeting PD-1 and/or PD-1 ligands), molecules that inhibit the cytotoxic T-lymphocyte-associated 4 protein (CTLA-4; e.g., antibodies targeting CTLA-4 such as ipilumumab), and molecules that inhibit lymphocyte-activation gene 3 (Lag3; e.g., antibodies targeting Lag3).

A composition including one or more UCP2 inhibitors can be administered to a mammal having a cancer and/or an infection as a combination therapy with one or more additional agents used to treat a cancer and/or an infection. For example, a combination therapy used to treat a mammal having a cancer can include administering to the mammal (e.g., a human) a composition including one or more UCP2 inhibitors and one or more anti-cancer treatments (e.g., radiation therapy, chemotherapy, targeted therapies, hormonal therapy, and/or angiogenesis inhibitors). For example, a combination therapy used to treat a mammal having an infection can include administering to the mammal (e.g., a human) a composition including one or more UCP2 inhibitors and one or more anti-microbials (e.g., antibiotics, antivirals, antifungals, and/or antiparasitics).

In embodiments where a composition including one or more UCP2 inhibitors and additional agents (e.g., co-stimulatory molecules, cytokines, antigen, and/or additional agents used to treat a cancer and/or an infection) are administered to a mammal, the one or more additional agents can be administered at the same time or independently. In some cases, the composition including one or more UCP2 inhibitors can be administered first, and the one or more additional agents administered second, or vice versa.

In some cases, one or more UCP2 inhibitors can be formulated into a pharmaceutically acceptable composition for administration to a mammal having a cancer and/or an infection. For example, a therapeutically effective amount of a UCP2 inhibitor can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more UCP2 inhibitors can be designed for oral or parenteral (including subcutaneous, intramuscular, intravenous, and intradermal) administration. When being administered orally, a pharmaceutical composition containing one or more UCP2 inhibitors can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including one or more UCP2 inhibitors can be administered locally or systemically. For example, a composition containing a UCP2 inhibitor can be administered systemically by an oral administration or by injection to a mammal (e.g., a human).

Effective doses can vary depending on the severity of the cancer and/or infection, the route of administration, the age and general health condition of the subject, excipient usage, the possibility of co-usage with other therapeutic treatments such as use of other agents, and the judgment of the treating physician.

An effective amount of a composition containing one or more UCP2 inhibitors can be any amount that reduces the severity of a symptom of a condition being treated (e.g., a cancer and/or an infection) without producing significant toxicity to the mammal. For example, an effective amount of a UCP2 inhibitor such as Genipin can be from about 200 mg/kg to about 600 mg/kg (e.g., from about 250 mg/kg to about 550 mg/kg, from about 275 mg/kg to about 500 mg/kg, from about 300 mg/kg to about 450 mg/kg, from about 325 mg/kg to about 425 mg/kg, or from about 350 mg/kg to about 400 mg/kg). The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., a cancer and/or an infection) may require an increase or decrease in the actual effective amount administered.

The frequency of administration can be any frequency that reduces the severity of a symptom of a condition to be treated (e.g., a cancer and/or an infection) without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing one or more UCP2 inhibitors can include rest periods. For example, a composition containing one or more UCP2 inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., a cancer and/or an infection) may require an increase or decrease in administration frequency.

An effective duration for administering a composition containing one or more UCP2 inhibitors can be any duration that reduces the severity of a symptom of the condition to be treated (e.g., a cancer and/or an infection) without producing significant toxicity to the mammal. For example, the effective duration can vary from several days to several weeks, months, or years. In some cases, the effective duration for the treatment of a cancer and/or an infection can range in duration from about one month to about 10 years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the condition being treated (e.g., a cancer and/or an infection) can be monitored. Any appropriate method can be used to determine whether or not the severity of a symptom is reduced. For example, the severity of a symptom of cancer can be assessed using imaging technologies (x-rays, CAT scans, and/or bone scans) and/or biopsies (e.g., tissue biopsies and/or liquid biopsies) at different time points.

A composition containing one or more UCP2 inhibitors can be combined with packaging material and sold as a kit. The packaging material included in a kit typically contains instructions or a label describing how the composition can be used, for example, to increase an ex vivo immune response in naïve CD8 T cells isolated from a mammal against an antigen present within the mammal. In some cases, a kit can also include a co-stimulatory molecule and/or a cytokine.

The invention will be further described in the following examples, which do not limit the scope of the invention described in the claims.

EXAMPLES

Example 1

Methods

Naïve or resting CD8+ T cells obtained from OT-1 PL Rag−/− TCR transgenic mice were stimulated in vitro with its cognate antigen in the presence of B7.1 co-stimulatory molecule, and cytokine IL-12 for 48h. The antigen constitutes sulfate latex microspheres (Life Technologies Cat. No. S37227) bearing DimerX Ig-recombinant dimeric mouse H-2Kb: Ig fusion protein (BD Biosciences, Cat. No. 550750) with recombinant mouse B7-1/CD80 Fc chimeric protein (R&D Systems, Cat. No. 740-B). Short synthetic peptide SIINFEKL (SEQ ID NO:1) at 10 nM concentration (sequence derived from a chicken ovalbumin protein), presented by H-2Kb DimerX serves as the cognate antigen for TCR of CD8+ T cells from OT-1 PL Rag−/−TCR transgenic mice. CD8+ T cells isolated from lymph nodes and/or spleen were stimulated with antigen in the following culture medium: Glutamine-free RPMI (Corning CellGro, Cat. No. 15-040-CV) supplemented with FBS 10%, HEPES 10 mM, NEAA 1 mM, sodium pyruvate 1 mM, glutamine 2 mM, 2-mercaptoethanol 50 μM, and Pen/Strep.

T cells were cultured in flat-bottom 96-well plates at 2×105/0.2 ml/well with microspheres at the ratio of 5:1. Genipin was added at 50 μM concentration (based on dose titration that produces minimal cell death) and preincubated with cells for 45 mins before subjecting the CD8+ T cells to antigen stimulation. The CD8+ T cells are cultured and harvested at 4 hours to 48 hours for evaluation by molecular, physiologic and phenotypic characteristics by standard methodologies like flow cytometry based phenotyping, lysis for protein or mRNA derivation using western blot, PCR and metabolic flux analysis.

For in vivo experiments, ex vivo conditioned OT-1 cells (with antigen plus or minus Genipin) were adoptively transferred into Thy 1.2 syngeneic C57BL/6 mice by tail vein injection. The presence of adoptively transferred conditioned OT-1 cells was evaluated at day 4 and 40 for long term persistence and survival.

To test for the ability of protection against tumor challenge, we adoptively transferred ex vivo conditioned OT-1 cells (with antigen plus or minus Genipin) into B16-OVA tumor bearing mice. Survival and tumor growth were monitored over a period of time based on IACUC (Mayo Clinic) approved criterion.

Example 2

UCP2 Expression in Naïve CD8+ T Cells

To characterize the regulatory role for antigen induced UCP2 expression in CD8+ T cell metabolic reprogramming, a reductionist in vitro approach was employed, which is amenable to molecular and physiological investigations. The in vitro system used naïve CD8+ T cells obtained from TCR transgenic mice (OT-1/Rag$^{-/-}$) mice that were provided three requisite signals.

Signal one was provided by MHC Class I (H-2Kb) dimers bearing 1-10 nM of OT-1 cognate peptide (SIINFEKL; SEQ ID NO:1) (Ag). Signal two was provided by 1 μg/ml of recombinant murine B7.1 (co-stimulation) immobilized on inert latex microspheres (serves as artificial antigen presenting cells) in the presence of the third signal; 2 ng/ml of rmIL-12 (cytokine). For antigen stimulation, the naïve T cells and latex microspheres were reacted at a ratio of 5:1 (T cells: microspheres) for various time points and were evaluated for their molecular, physiologic and phenotypic characteristics by standard methodologies including flow cytometry, western blot, PCR and metabolic flux analysis (FIG. 1).

Stimulation of naïve OT-1 cells with antigen induced UCP2 (mRNA and protein) expression was optimal at 24h and persisted up to 48h. The expression of UCP2 in CD8+ T cells was regulated by the strength of antigen signal (dose dependent; 1 to 10 nM) and required activation of mTORC1 kinase activity.

Figure 2:
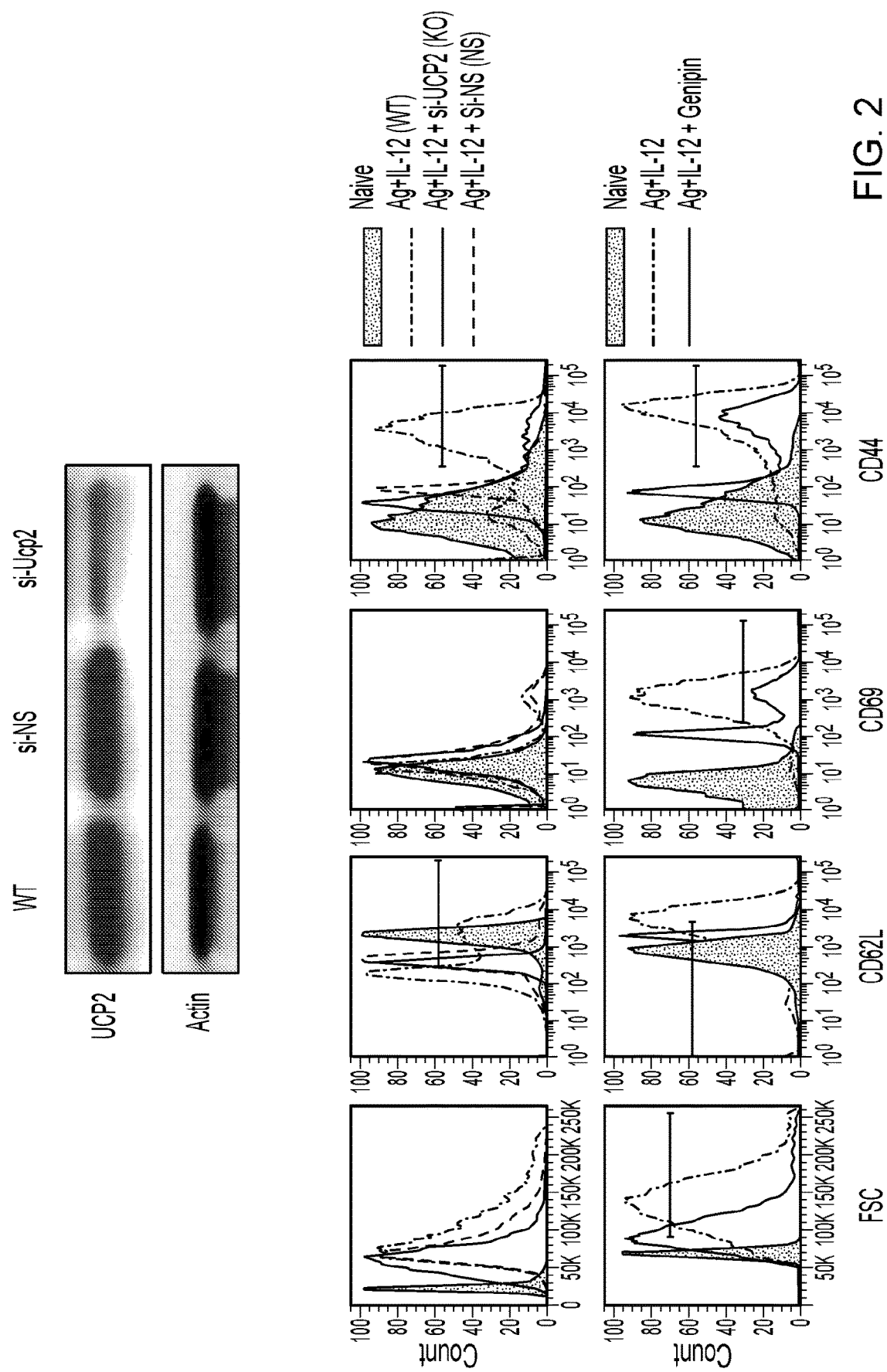
FIG. 2 shows that UCP2 is an essential gene for maintaining the balance in metabolic reprogramming required for CD8+ T cell functional maturation.

UCP2 inhibition decreased expression of CD62L (FIG. 2), suggesting that UCP2 is an essential gene for maintaining the balance in metabolic reprogramming required for CD8+ T cell functional maturation.

These results demonstrated that antigen stimulation induces UCP2 expression in naïve CD8+ T cells.

Example 2

UCP2 and Mitochondrial ROS for CD8+ T Cell Clonal Expansion

To determine whether UCP2 plays a role in antigen induced ROS generation and determine its impact on CD8+ T cell clonal expansion, antigen induced cytoplasmic (CROS) and/or mitochondrial ROS (mROS) production was evaluated by CM-H2DCFDA and MitoSox staining and flow cytometry analysis, respectively. Genetic (si-UCP2) or pharmacological (Genipin) means were used to block UCP2 function.

Figure 3A:
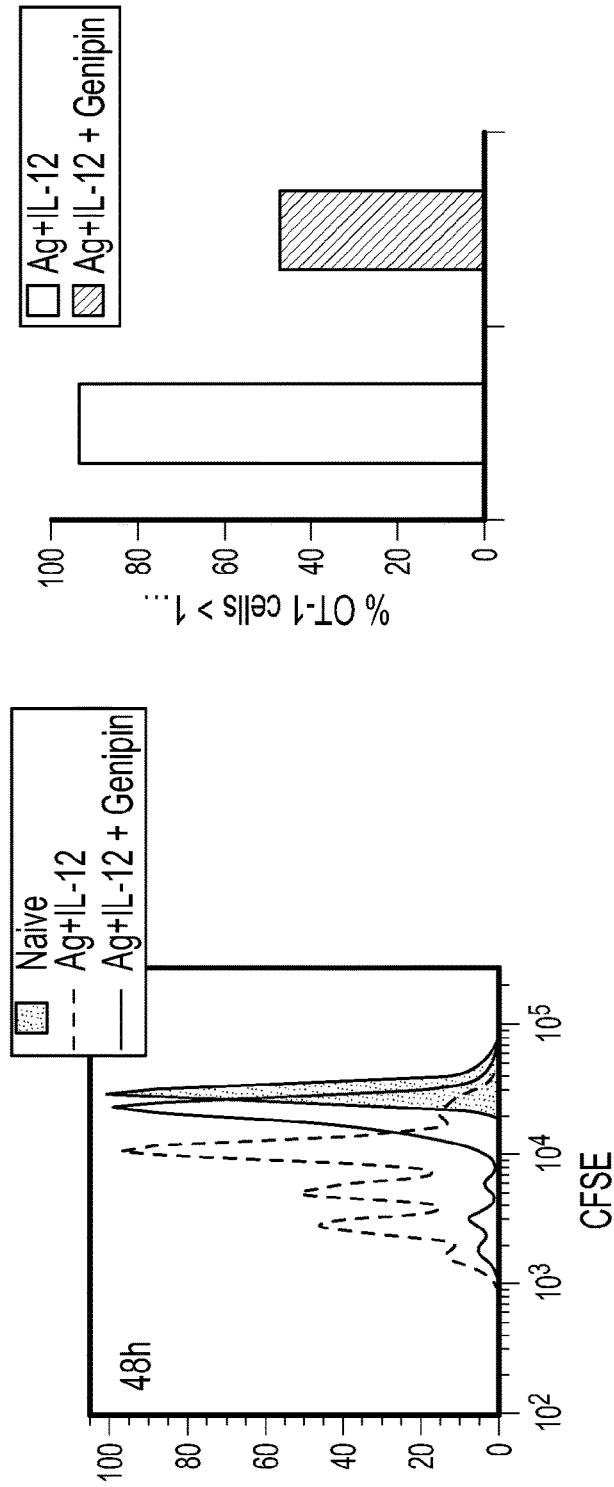
FIGS. 3A-C show that UCP2 dampens mitochondrial ROS to restrict apoptosis and CD8+ T cell contraction. A) UCP2 activity is required for clonal expansion of CD8+ T cells. B) UCP2 dampens mitochondrial ROS to restrict apoptosis and CD8+ T cell contraction. C) UCP2 increases CD8+ T cell clonal expansion by restricting apoptosis.
Figure 3A:
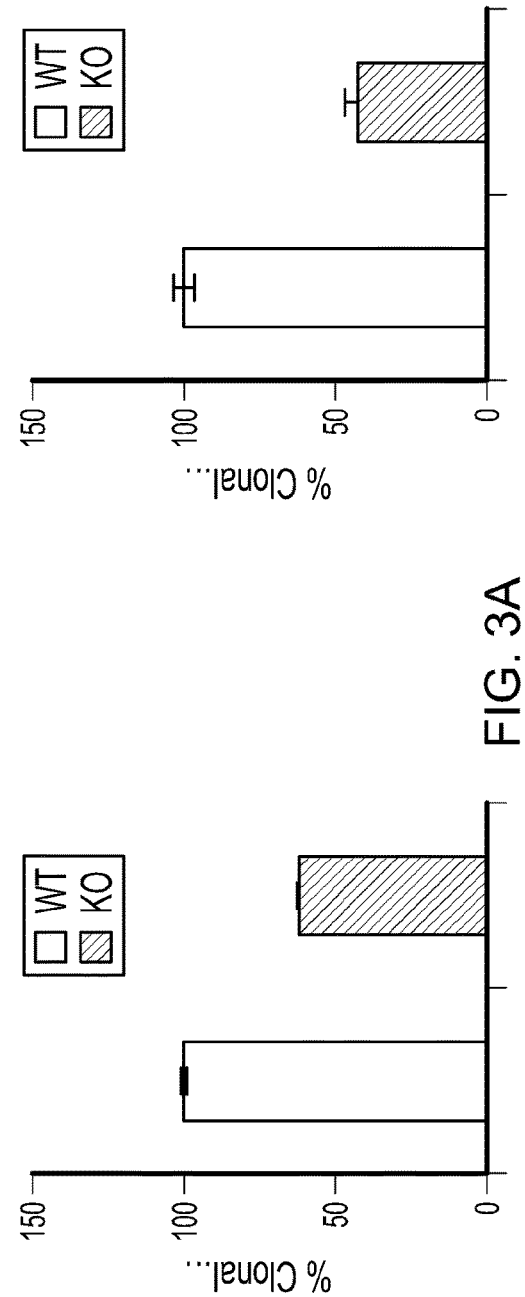
Figure 3A:
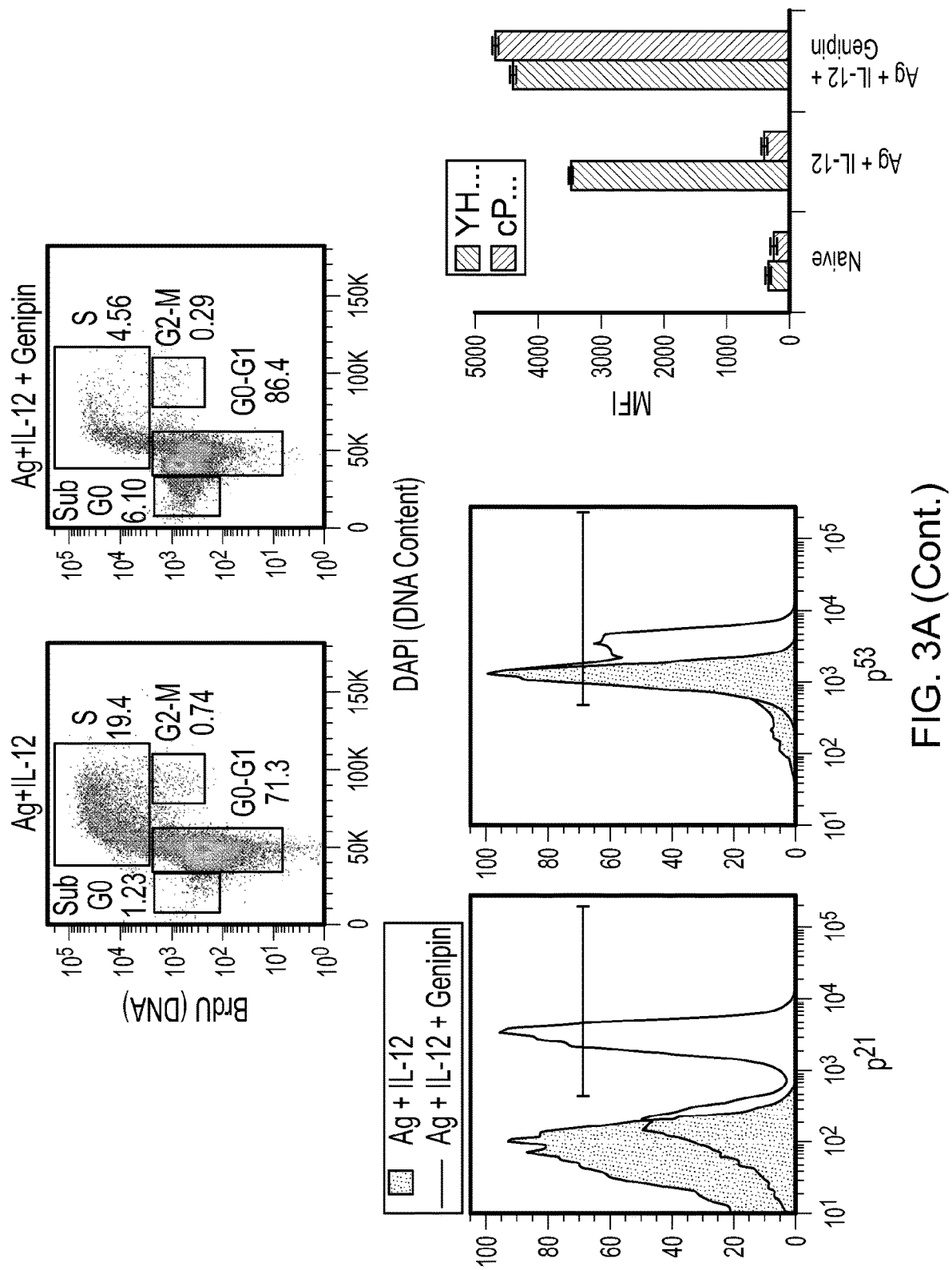

Genipin treated activated CD8+ T cells undergo limited proliferation (FIG. 3A), due to slower progression through the cell cycle.

Figure 3B:
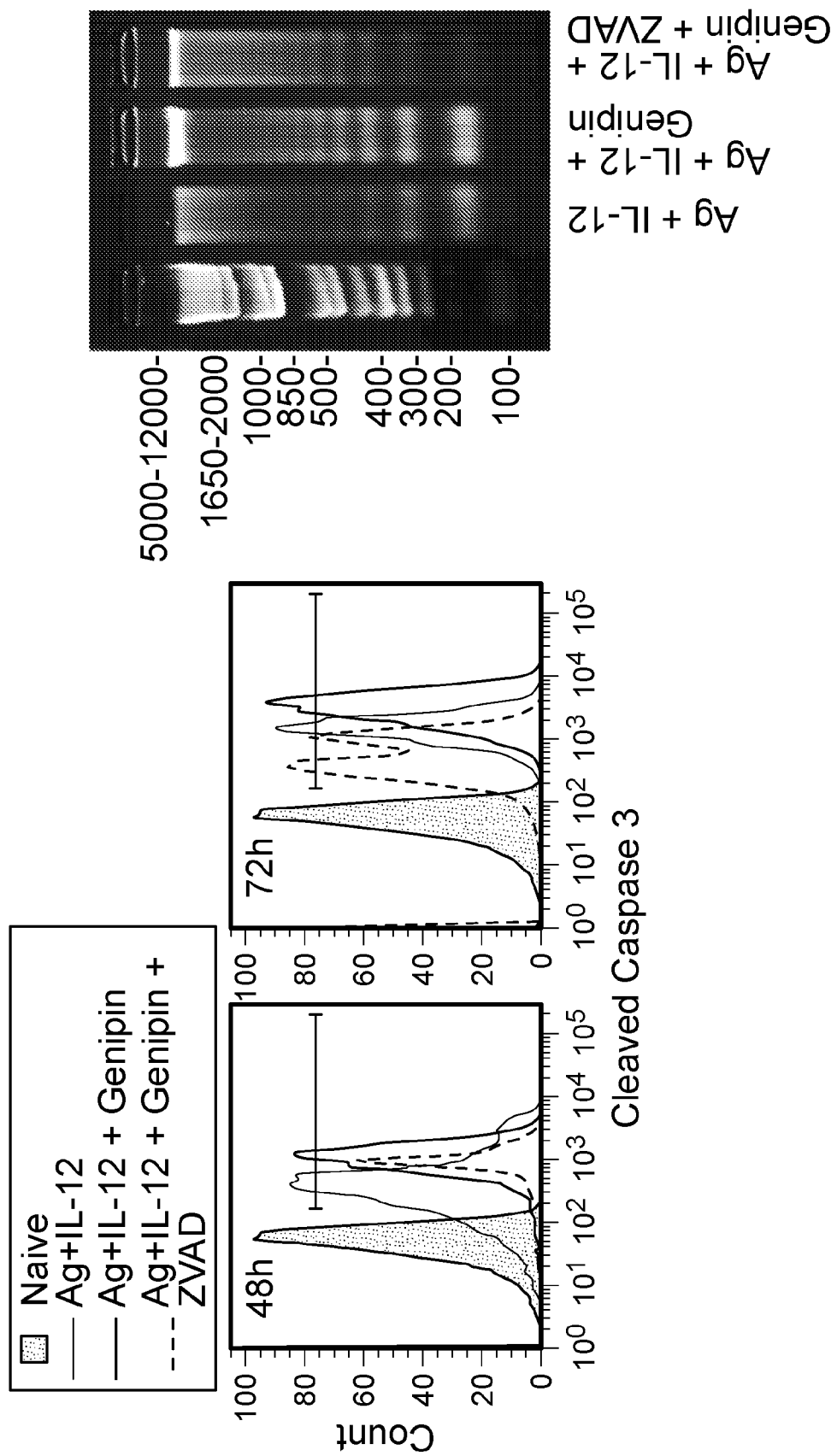
Figure 3B:
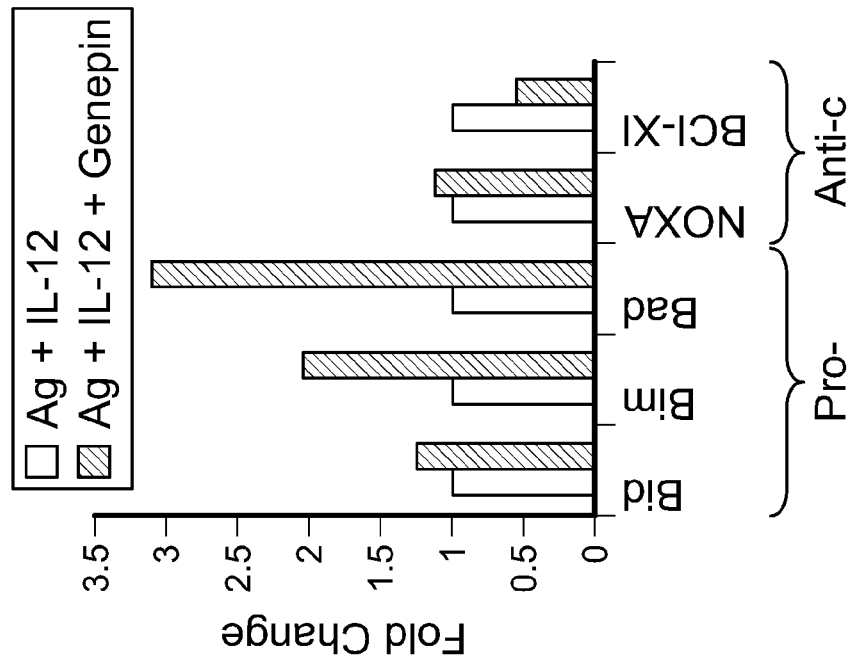
Figure 3B:
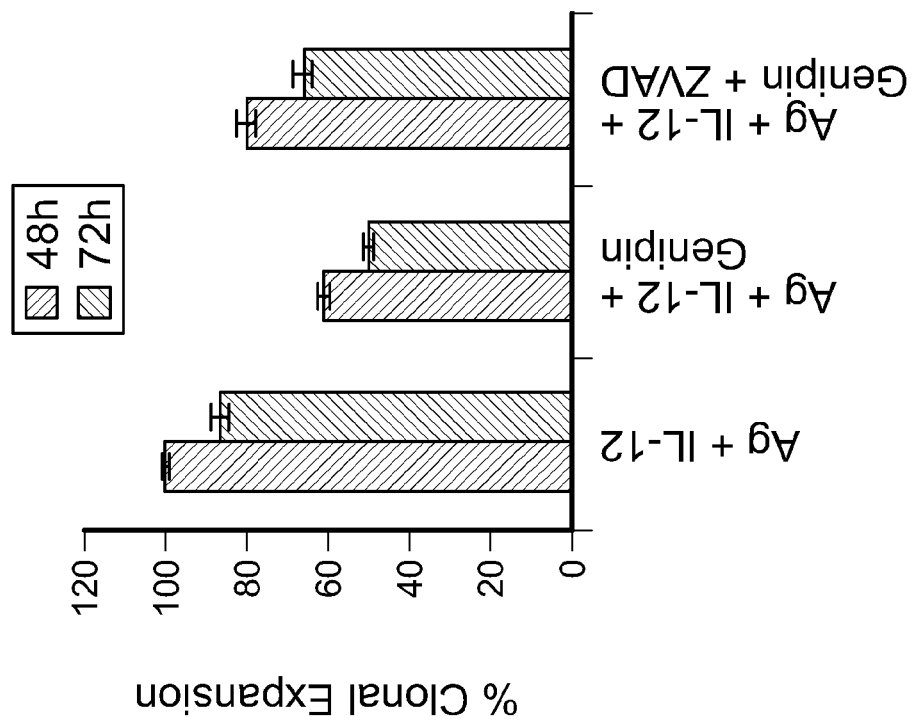

Contraction in clonal expansion with Genipin is a result of increased apoptosis and can be reversed on addition of pan caspase inhibitor ZVAD (FIG. 3B). Since Genipin targets UCP2, an increase in mitochondrial reactive oxygen species (ROS) was observed.

Figure 3C:
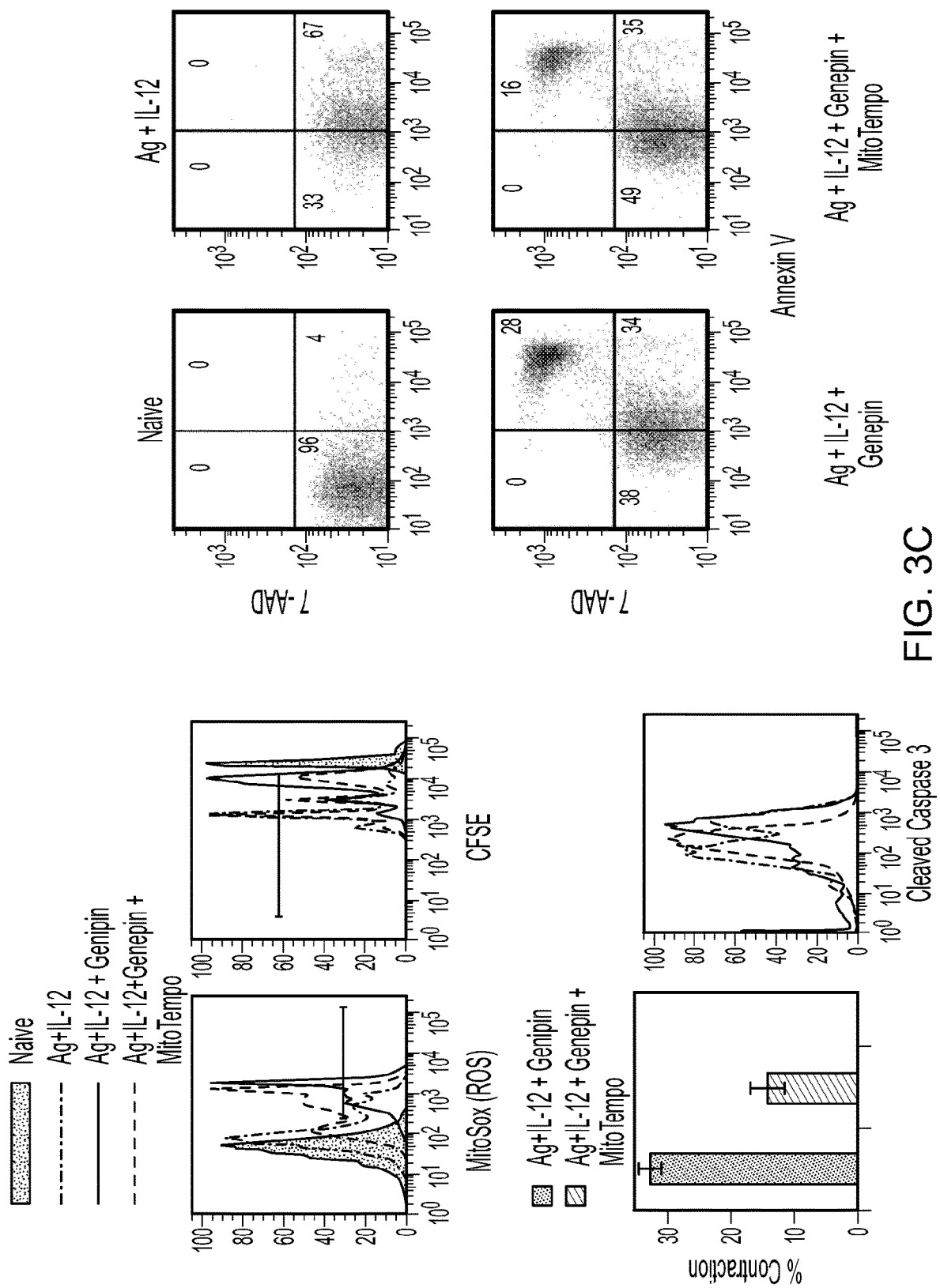

Inhibition of UCP2 in antigen stimulated OT-1 cells produced a significant increase in mROS (MitoSox fluorescence), but no significant cROS (CM-H2DCFDA) differences were noted. The higher levels of mROS were correlated with lower expansion of CD8+ T cells as well as induction of apoptotic gene expression; Bim, Bad. Quenching of mitochondrial ROS using a mitochondrially targeted antioxidant, MitoTempo (Enzo Life Sciences) reverses ROS and restored cell proliferation and cell contraction (FIG. 3C).

These results demonstrated that UCP2 dampens mitochondrial ROS to restrict apoptosis and CD8+ T cell contraction.

Example 3

UCP2 and Metabolic Reprogramming for CD8+ T Cell Differentiation

Figure 4A:
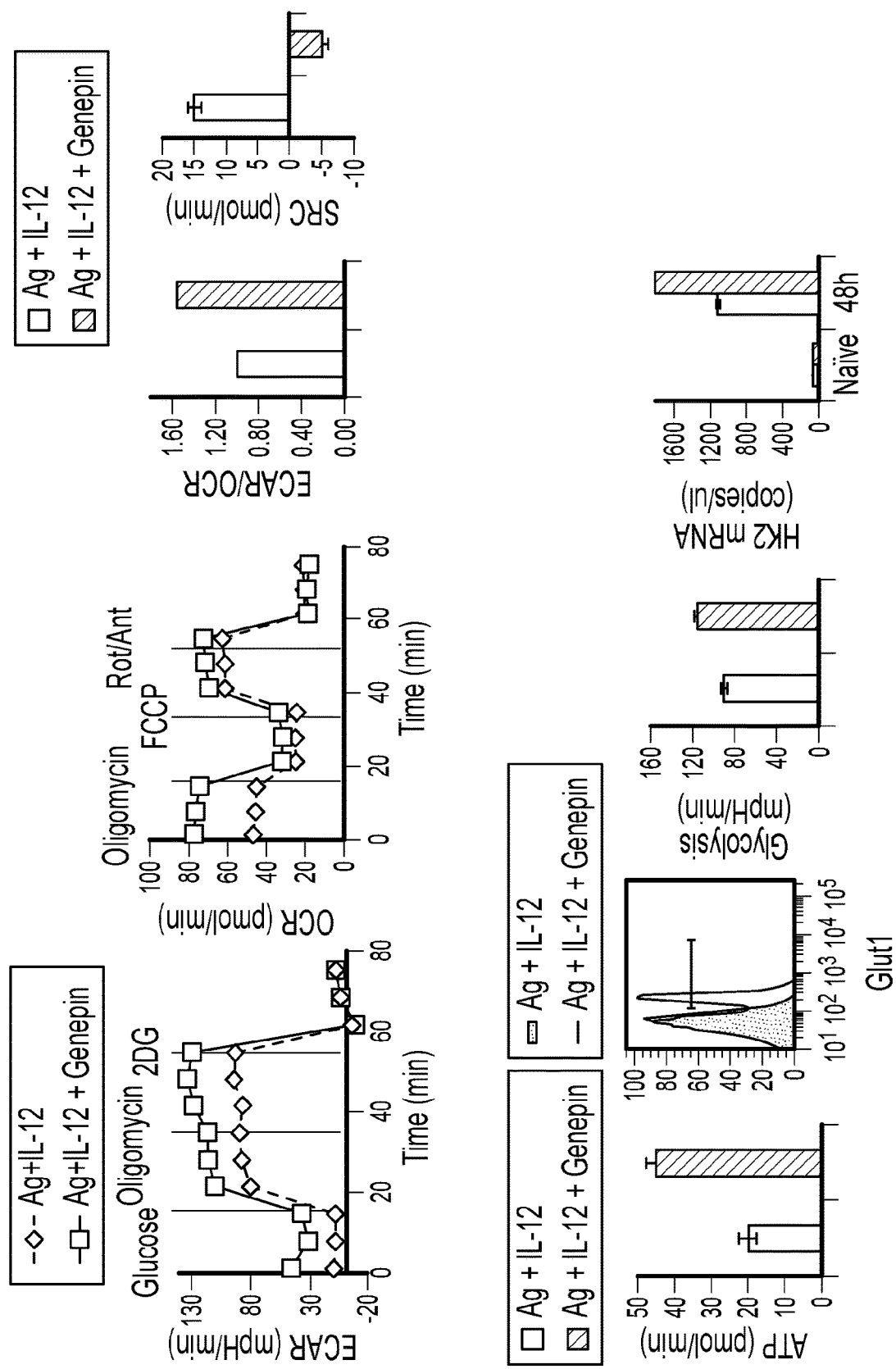
FIGS. 4A-D show that UCP2 balances metabolic reprogramming for CD8+ T cell differentiation. A) UCP2 regulates metabolic programming to maintain spare respiratory capacity (SRC). B) UCP2 inhibition induces substrate switching for de novo lipogenesis. C) Loss of UCP2 increases dependency on glucose availability. D) Citrate transport is required for de novo lipogenesis and survival of UCP2 inhibited cells.
Figure 4B:
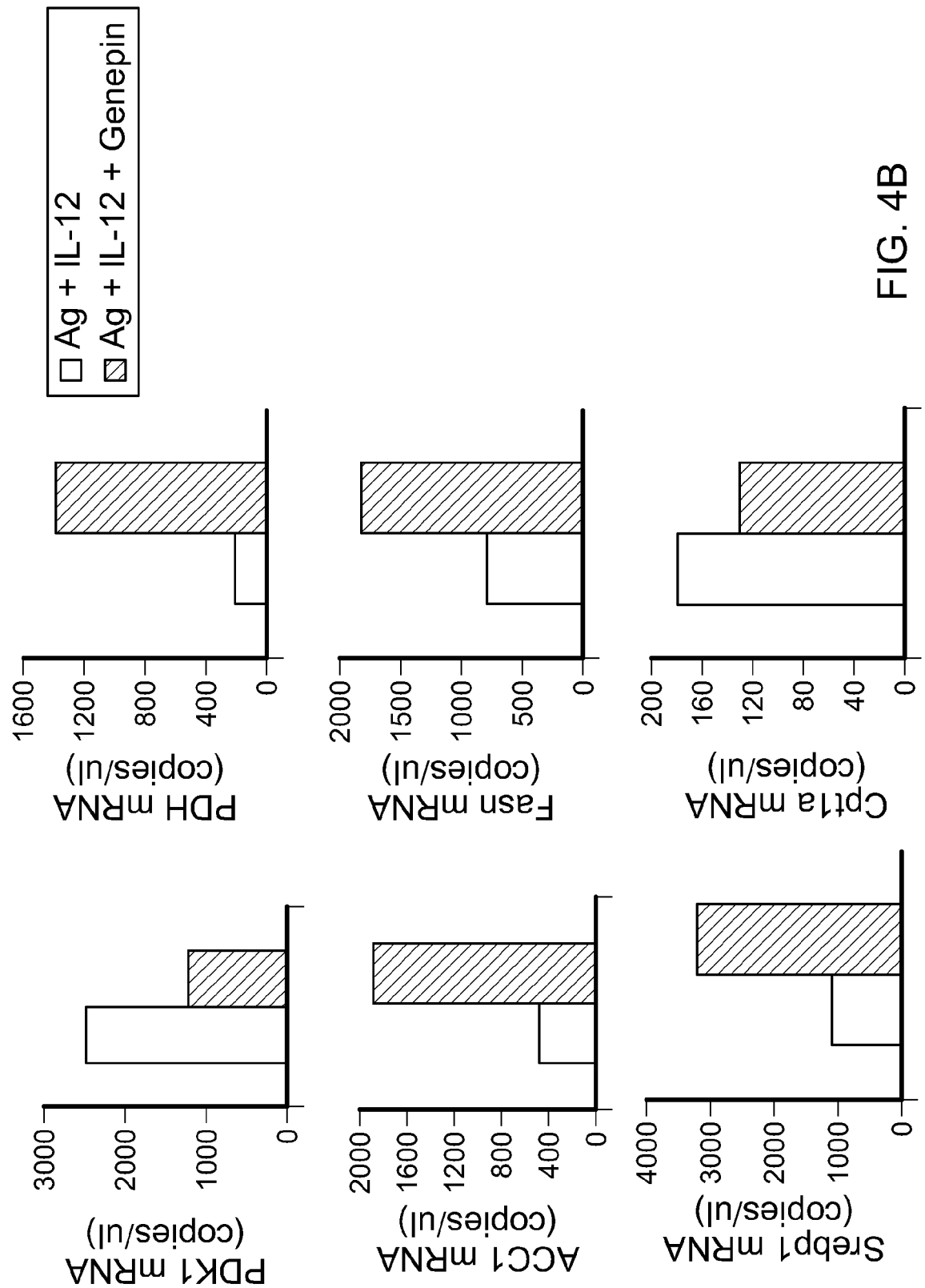
Figure 4B:
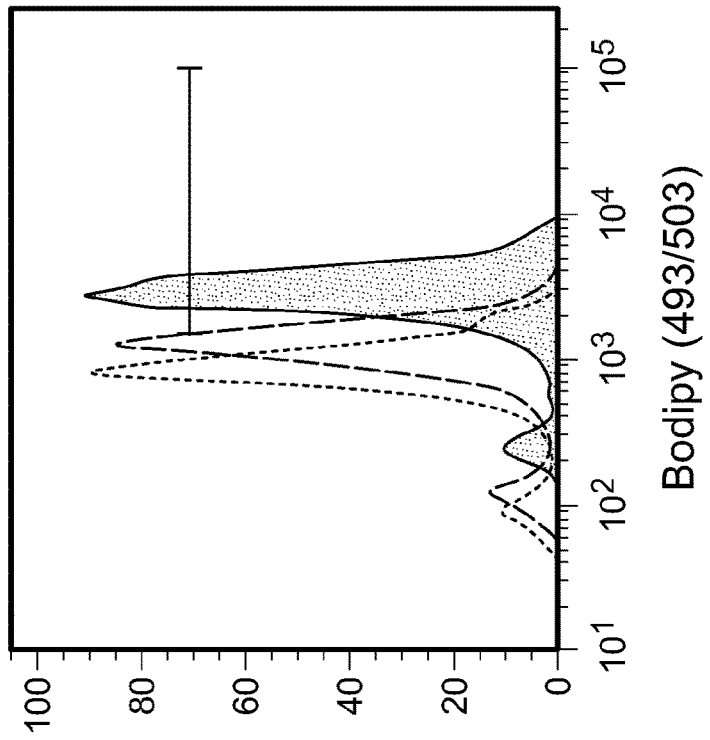
Figure 4B:
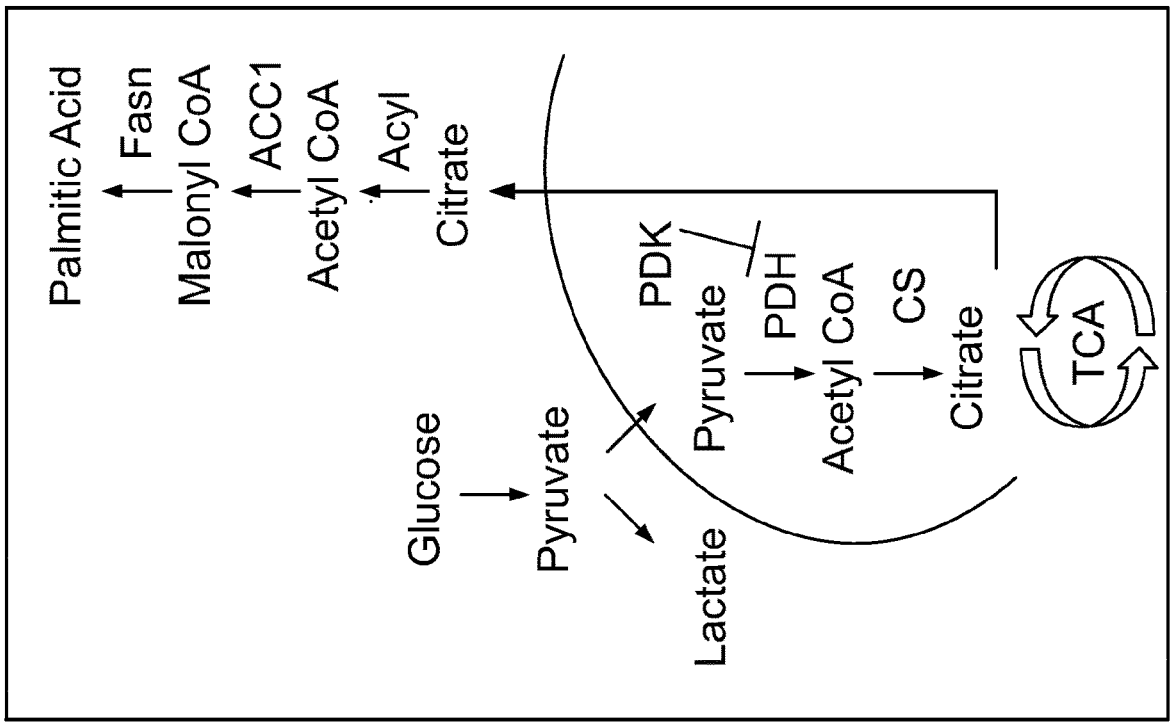
Figure 4C:
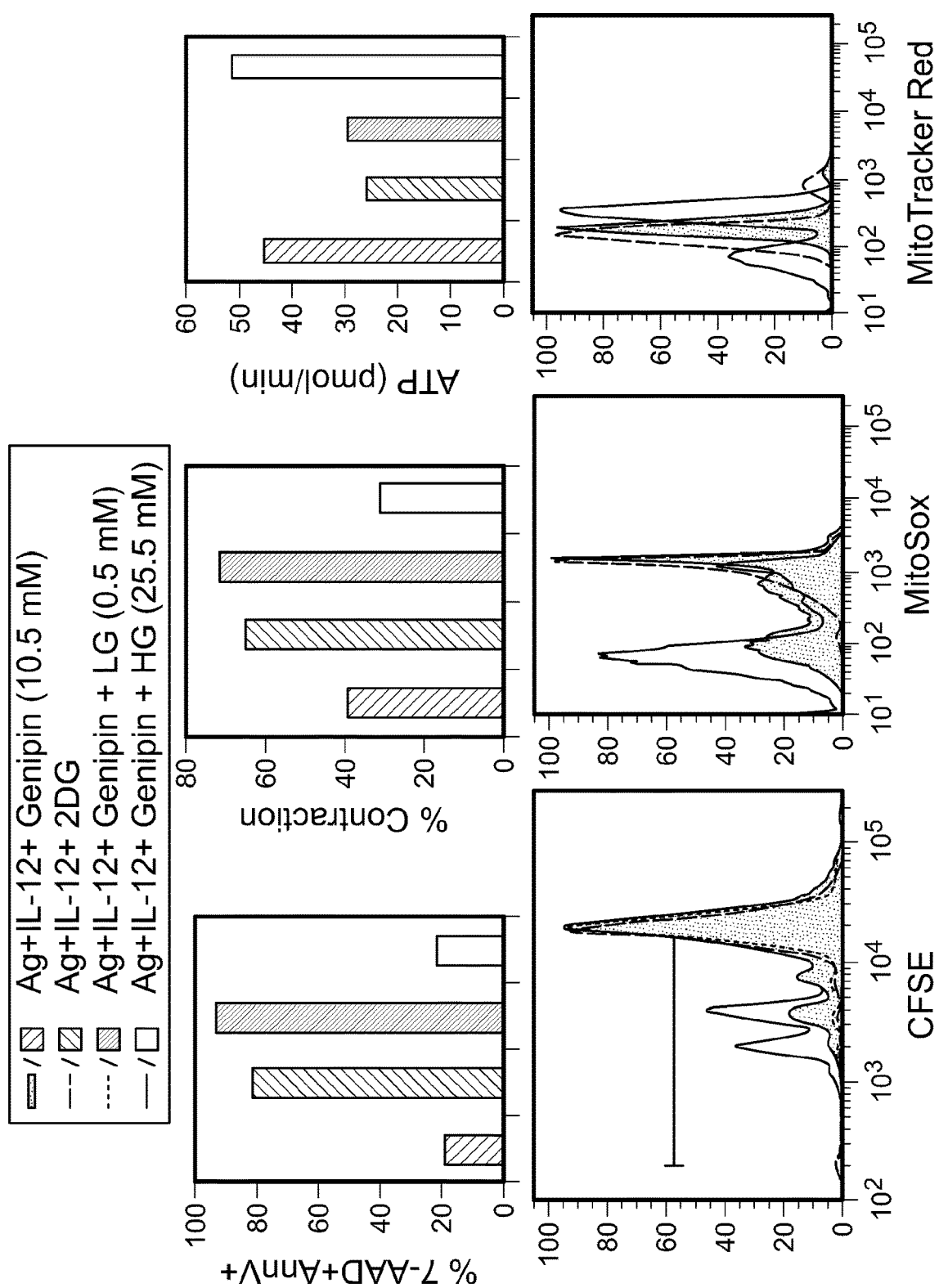
Figure 4D:
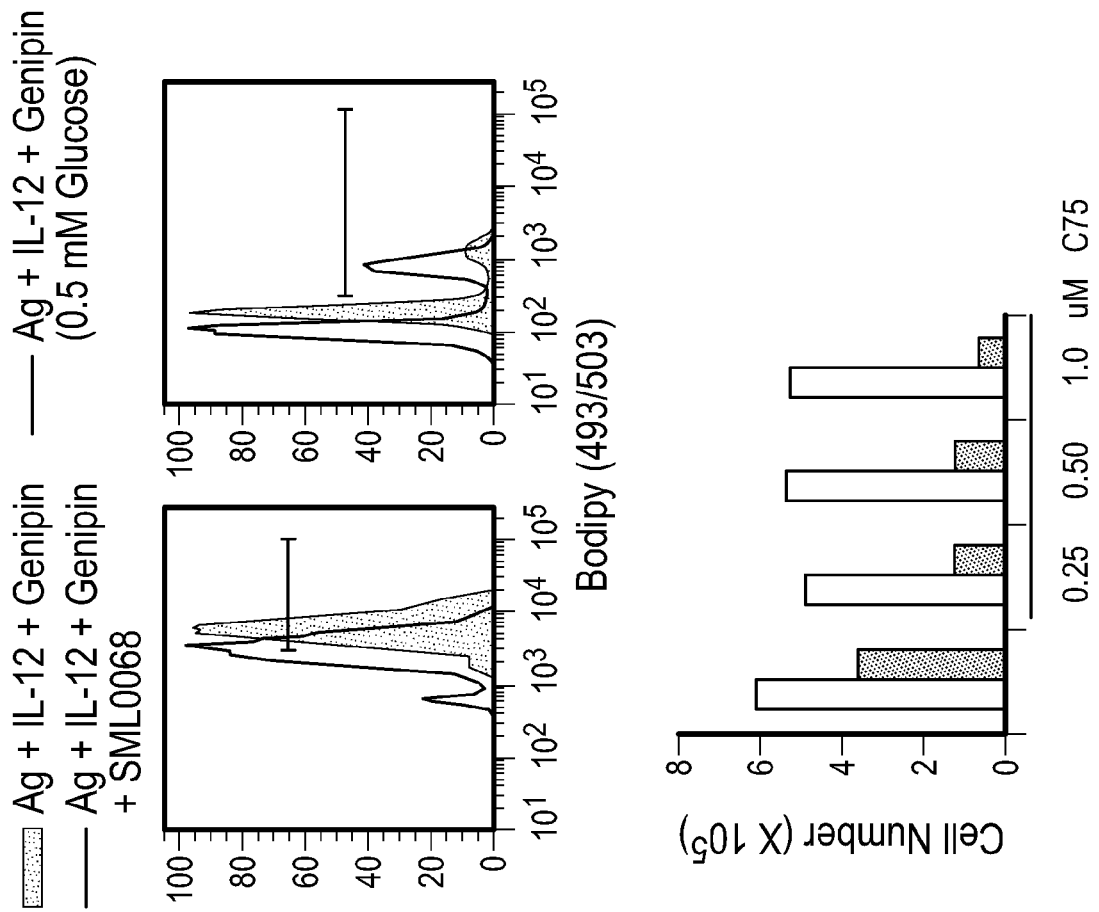
Figure 4D:
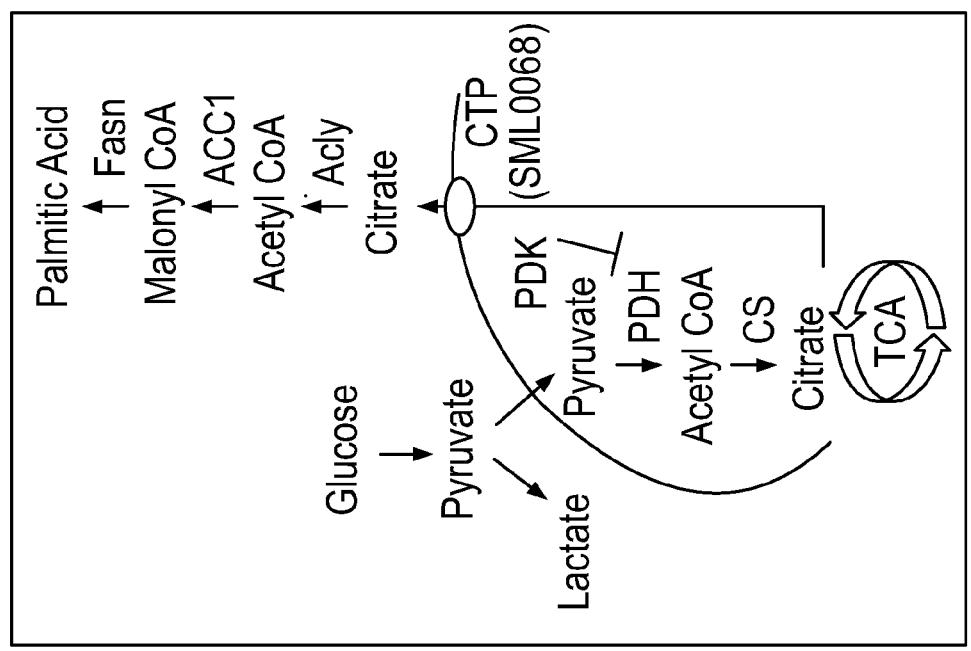
Figure 4D:
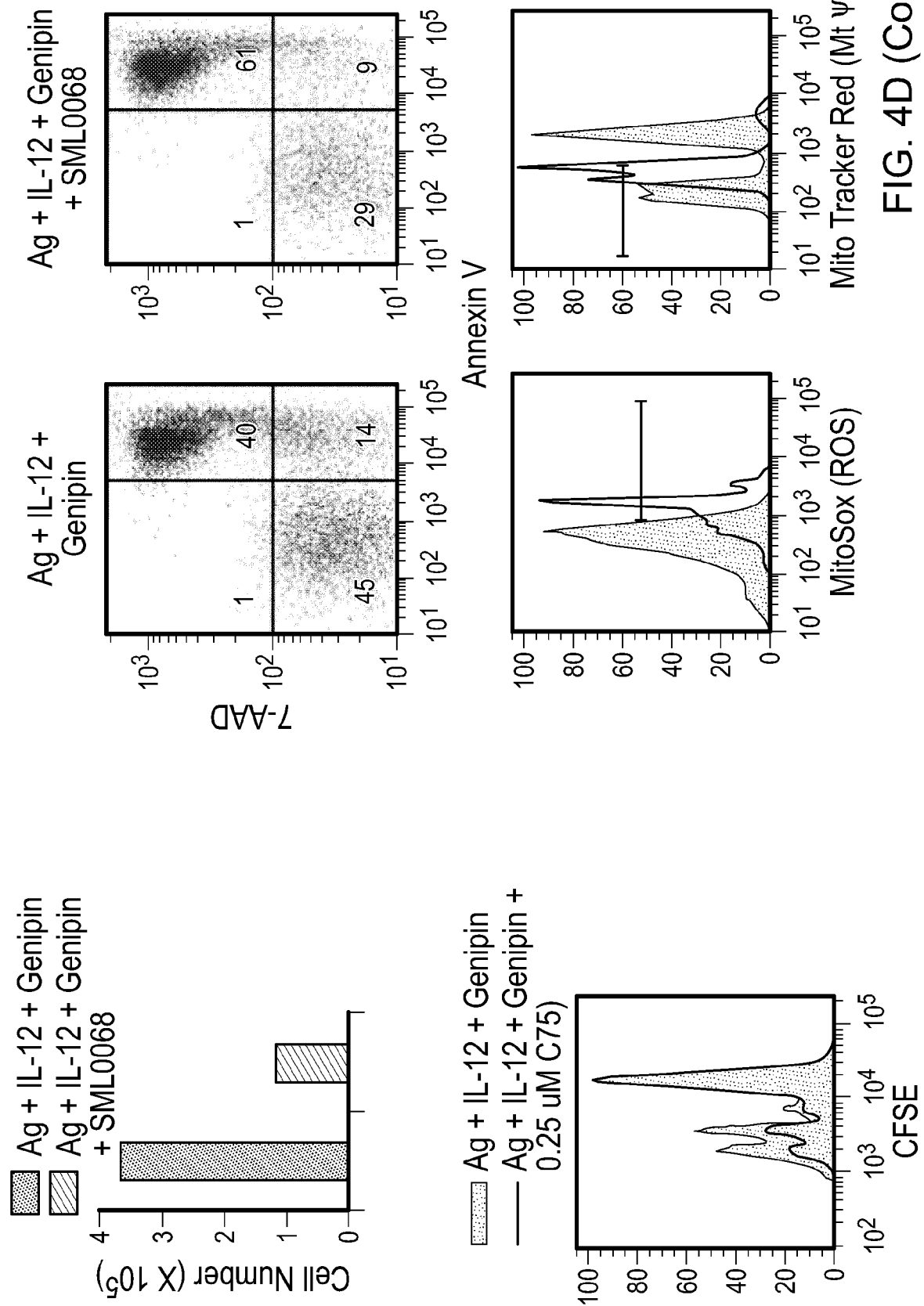

Antigen stimulation of CD8+ T cells in the presence of Genipin induces metabolic reprogramming to favor glycolysis over mitochondrial respiration (FIG. 4A) was indicated by the higher ECAR/OCR ratio. These cells possessed very low spare respiratory capacity (SRC), which is the extra mitochondrial reserve available to a cell to produce energy under conditions of stress and was reflective of long term persistence and survival typically seen in memory T cells. Low SRC is often deemed as a metabolic marker of terminally differentiated effector cells. Increased glycolysis was accompanied by increased lipid content requiring de novo lipid synthesis (FIG. 4B). Lipid synthesis was dependent on glucose availability and sustained glycolysis, in the absence of glycolysis a decline in fatty acid synthesis was observed (FIG. 4C). Conversion and export of citrate derived from glucose oxidized pyruvate was essential to maintain lipid synthesis. Blocking the cytoplasmic export of citrate from the mitochondria using citrate transport inhibitor, SML0068 reduced lipid synthesis (FIG. 4D).

These results demonstrated that UCP2 balances metabolic reprogramming for CD8+ T cell differentiation.

Example 4

UCP2 and Terminal Differentiation

Figure 5:
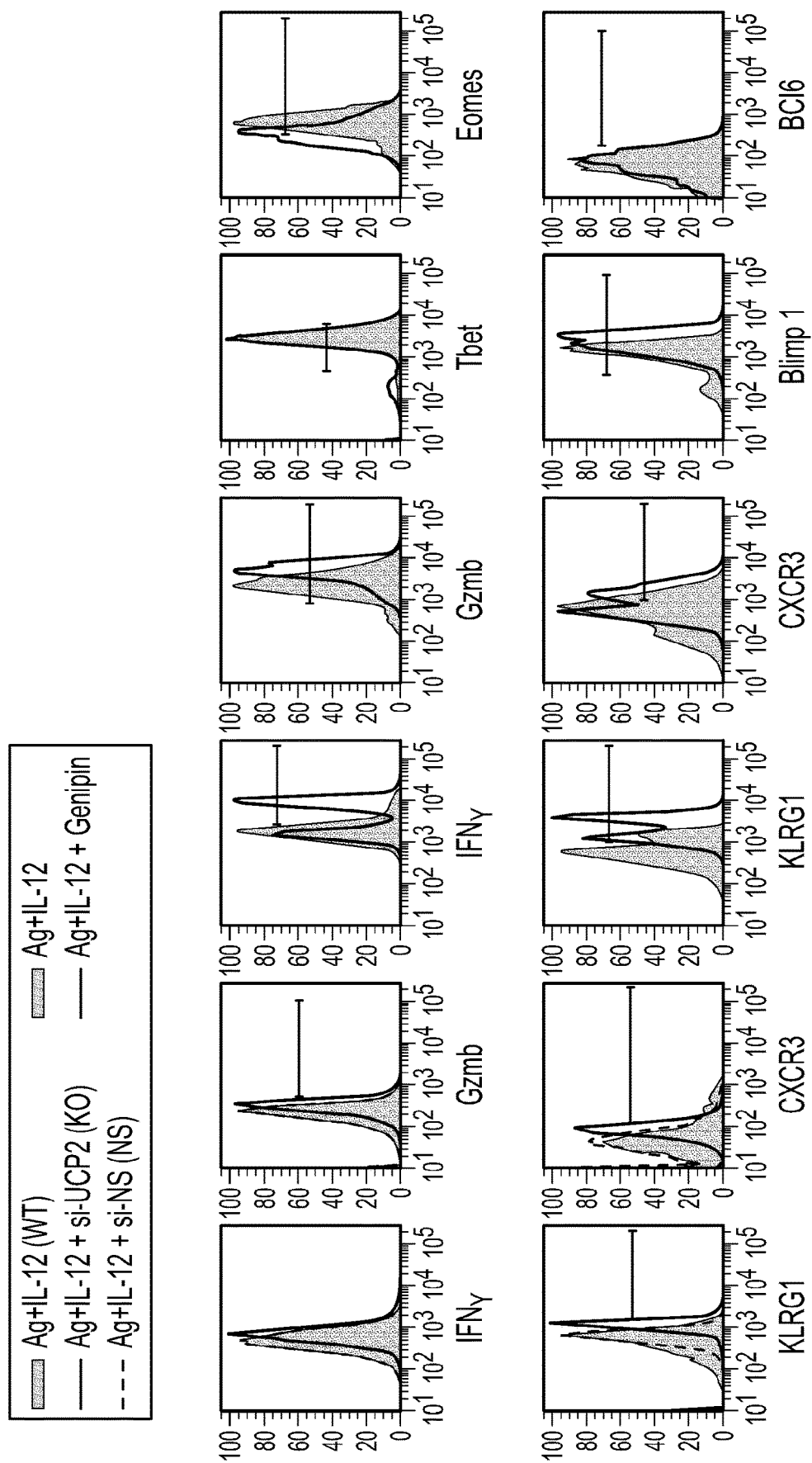
FIG. 5 shows that UCP2 inhibition enhances CD8+ effector differentiation.

UCP2 inhibition increased expression of IFNγ, Gzmb, and effector cell markers KLRG1 and CXCR3 (FIG. 5) indicating that CD8+ T cells treated with Genipin express markers typical of differentiated effector cells, more specifically, high levels of cytolytic factors. Genipin also changed the transcription landscape in CD8+ T cells towards terminally differentiated effector cell phenotype by increasing Tbet/Eomes ratio as well as Blimp1/BC16 ratio (FIG. 5). Furthermore, the robust effector differentiation also leads to increases in PD-1 and Lag3 expression indicating their terminal differentiation status.

These results demonstrated that UCP2 inhibition enhances CD8+ effector differentiation.

Example 5

UCP2 Inhibitors in Adoptive Cell Therapy

Figure 6A:
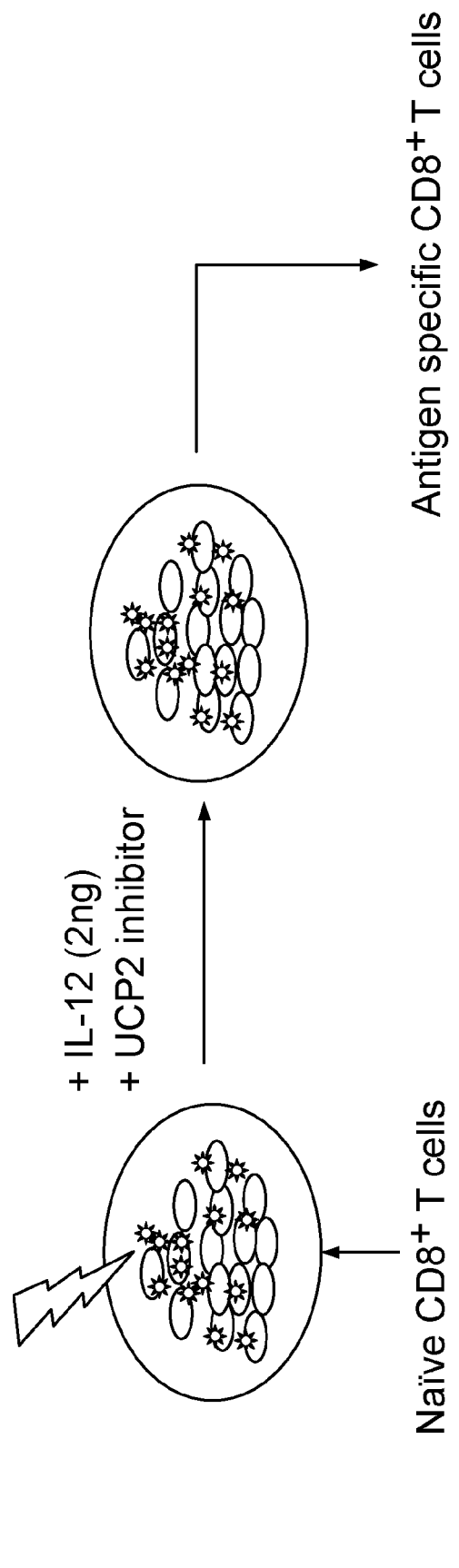
FIGS. 6A-B show UCP2 inhibition in adoptive cell therapy. A) Naïve CD8+ T cells were treated with antigen, co-stimulatory molecules, cytokines, and UCP2 inhibitors to produce antigen specific CD8+ T cells. B) UCP2 inhibition decreases persistence but increases CD8+ cytolytic function, and prevented tumor formation.
Figure 6B:
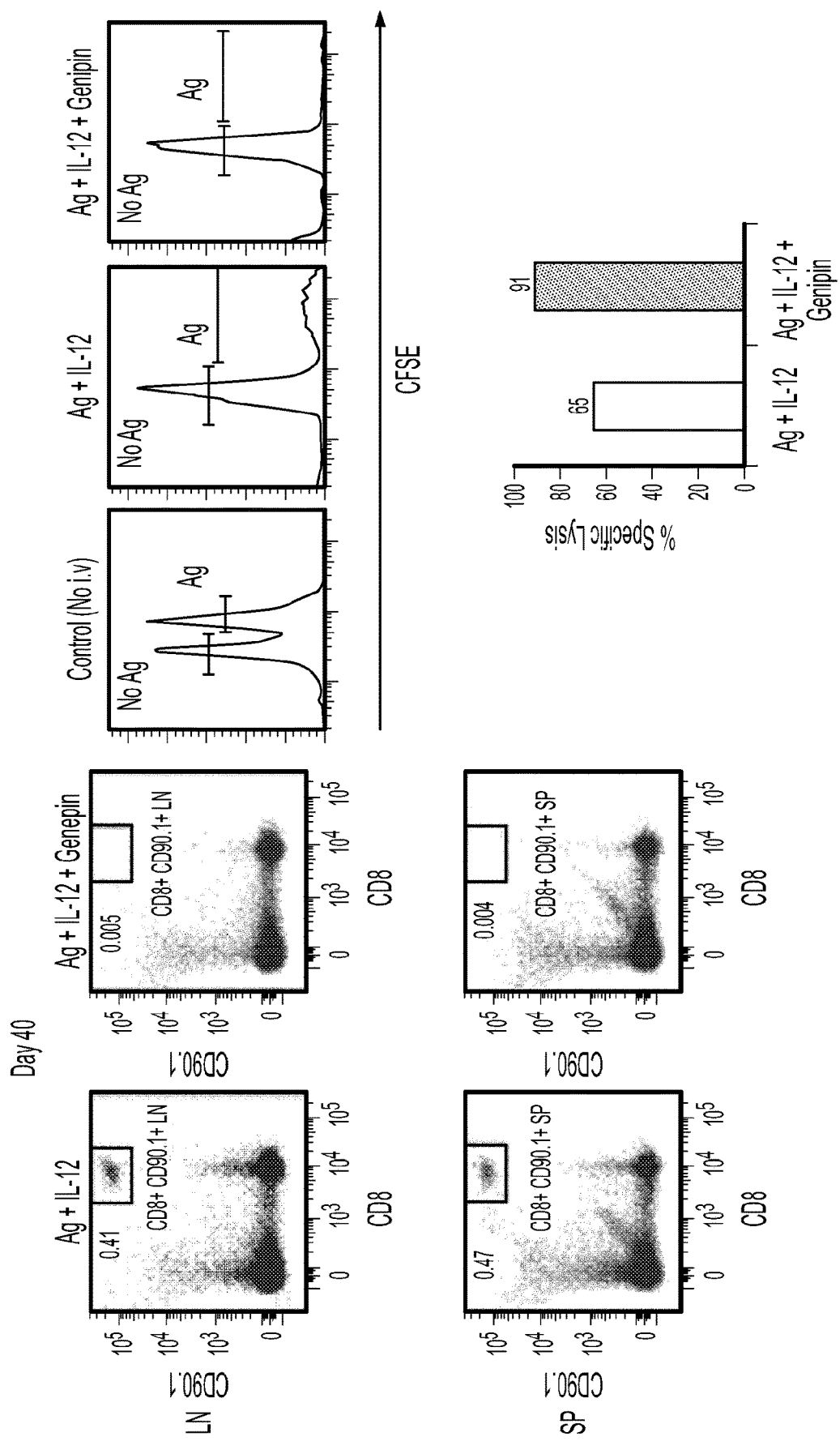
Figure 6B:
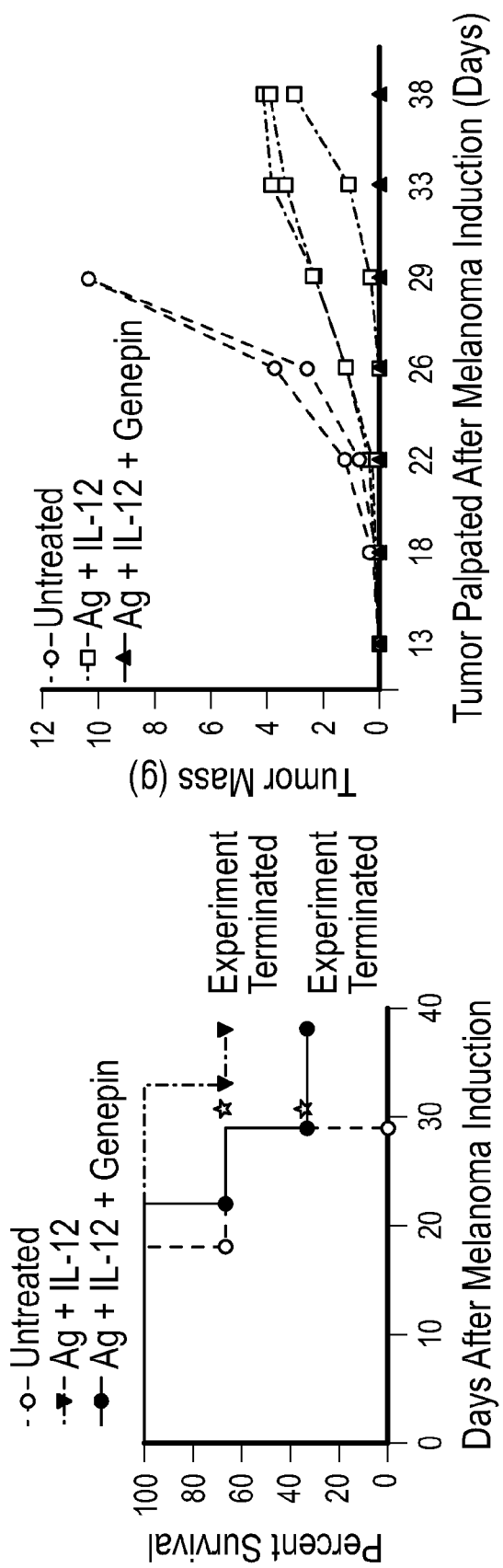

An adoptive cell therapy procedure is shown in FIG. 6A. These cells exhibit an increase in vivo cytolytic activity c, whereby enabling greater efficacy upon adoptive transfer into syngeneic mice against tumor by restricting B16-OVA growth; a murine model for melanoma (FIG. 6B).

These results demonstrated that UCP2 inhibitors can be used to condition CD8+ T cells for desired functional maturation, and can be used in adoptive cell therapy for treatment of cancer and infections.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

---

---

What is claimed is:

1. A method for treating cancer in a mammal, said method comprising:
   (a) contacting a tumor associated antigen, a co-stimulatory molecule selected from the group consisting of B7.1, CD28, and inducible co-stimulator (ICOS), a cytokine selected from the group consisting of IL-12, IL-2, and IFN-γ, and a UCP2 inhibitor to naïve CD8+T cells obtained from said mammal to generate effector CD8+T cells specific for the antigen ex vivo; and
   (b) administering the antigen specific effector CD8+T cells to said mammal.

2. The method of claim 1, wherein said cancer is breast cancer and said tumor associated antigen is MUC-1 or ETA.

3. The method of claim 1, wherein said mammal is a human.

4. The method of claim 1, wherein said UCP2 inhibitor is Genipin or siRNA.

5. A method of generating antigen specific CD8+T cells ex vivo, said method comprising contacting a tumor associated antigen, a co-stimulatory molecule selected from the group consisting of B7.1, CD28, and ICOS, a cytokine selected from the group consisting of IL-12, IL-2, and IFN-γ, and a UCP2 inhibitor to nave CD8+T cells obtained from a mammal.

6. The method of claim 5, further comprising expanding the antigen specific T cells.

7. The method of claim 5, wherein said mammal is a human.

8. The method of claim 5, wherein said mammal has a cancer.

9. The method of claim 8, wherein said cancer is breast cancer and said tumor associated antigen is MUC-1 or ETA.

10. The method of claim 5, wherein said UCP2 inhibitor is Genipin or siRNA.

11. The method of claim 5, wherein said co-stimulatory molecule is B7.1.

12. The method of claim 5, wherein said cytokine is IL-12.

13. An antigen specific T cell obtained by the method of claim 5.

14. The method of claim 1, wherein said co-stimulatory molecule is B7.1.

15. The method of claim 1, wherein said cytokine is IL-12.

\* \* \* \* \*

UNITED STATES PATENT AND TRADEMARK OFFICE
CERTIFICATE OF CORRECTION

PATENT NO. : 11,141,432 B2
APPLICATION NO. : 16/081298
DATED : October 12, 2021
INVENTOR(S) : Protul Shrikant and Leena Chaudhuri Page 1 of 1

It is certified that error appears in the above-identified patent and that said Letters Patent is hereby corrected as shown below:

In the Claims

In Column 10, Line 54, in Claim 1, delete "CD8+T" and insert -- CD8+ T --.

In Column 10, Line 56, in Claim 1, delete "CD8+T" and insert -- CD8+ T --.

In Column 10, Line 57, in Claim 1, delete "CD8+T" and insert -- CD8+ T --.

In Column 10, Line 65, in Claim 5, delete "CD8+T" and insert -- CD8+ T --.

In Column 11, Line 3, in Claim 5, delete "nave" and insert -- naïve --.

In Column 11, Line 3, in Claim 5, delete "CD8+T" and insert -- CD8+ T --.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*